(12) United States Patent
Chang et al.

(10) Patent No.: US 6,350,620 B2
(45) Date of Patent: Feb. 26, 2002

(54) METHOD FOR PRODUCING MICRO-CARRIER AND TEST METHOD BY USING SAID MICRO-CARRIER

(75) Inventors: Rong-Seng Chang; Yu-Chan Chao, both of Taipei (TW)

(73) Assignee: Genemaster Lifescience Co., LTD, Chungho (TW)

(*) Notice: Subject to any disclaimer, the term of this patent is extended or adjusted under 35 U.S.C. 154(b) by 0 days.

(21) Appl. No.: 09/728,317

(22) Filed: Dec. 1, 2000

(30) Foreign Application Priority Data

May 12, 2000 (TW) ........................ 89109106 A

(51) Int. Cl.[7] .................. G01N 33/53; G01N 33/543; G01N 21/00; B05D 7/00; C23F 1/00

(52) U.S. Cl. .................. 436/518; 436/523; 436/524; 436/525; 436/527; 436/528; 436/533; 436/534; 436/43; 436/63; 436/164; 436/166; 436/170; 436/172; 436/805; 436/823; 436/177; 435/6; 435/7.1; 435/7.9; 435/7.92; 435/174; 435/176; 435/177; 435/961; 435/969; 435/970; 427/10; 427/133; 427/154; 427/160; 427/212; 427/214; 427/215

(58) Field of Search ...................... 216/2, 12, 13, 216/33, 36, 37, 40, 41, 83, 84, 95, 96, 100; 205/70, 81, 87, 93, 118, 135, 189, 205, 210, 223, 271, 316, 317, 334, 640, 666, 717, 775, 920, 921; 435/6, 7.1, 7.9, 7.92, 174, 175, 176, 177, 178–182, 961, 969, 970; 436/518, 523, 524–535, 43, 63, 164, 166, 169, 170, 172, 805, 807, 808, 823; 427/8, 10, 133, 154, 160, 212, 214, 215, 217, 220, 256, 259, 271, 272, 282, 307, 337, 402

(56) References Cited

U.S. PATENT DOCUMENTS

| | | | |
|---|---|---|---|
| 4,727,014 A | * | 2/1988 | Horn et al. .................. 430/521 |
| 5,118,369 A | * | 6/1992 | Shamir ........................ 156/64 |
| 5,306,466 A | * | 4/1994 | Goldsmith .................. 422/58 |
| 5,314,829 A | * | 5/1994 | Coles ........................ 436/165 |
| 5,807,523 A | * | 9/1998 | Watts et al. .................. 422/64 |
| 5,958,704 A | * | 9/1999 | Starzl et al. ................. 435/7.1 |
| 5,985,356 A | * | 11/1999 | Schultz et al. ................ 427/8 |
| 6,025,129 A | * | 2/2000 | Nova et al. .................... 435/6 |
| 6,068,966 A | * | 5/2000 | Koga .......................... 430/322 |
| 6,096,496 A | * | 8/2000 | Frankel ........................ 435/4 |
| 6,232,066 B1 | * | 5/2001 | Felder et al. .................. 435/6 |
| 6,248,540 B1 | * | 6/2001 | Weinberg et al. ............. 435/7.1 |
| 6,261,782 B1 | * | 7/2001 | Lizardi et al. ................. 435/6 |

FOREIGN PATENT DOCUMENTS

GB  2 240 948 A  *  8/1991

* cited by examiner

Primary Examiner—Long V. Le
Assistant Examiner—Kartic Padmanabhan
(74) Attorney, Agent, or Firm—Darby & Darby

(57) ABSTRACT

The invention provides a method for producing a micro-carrier, which includes patterning pluralities of bar code on a mask; exposing the bar code to a substrate coated with photoresist; etching and removing residual photoresist and electroforming to a nickel plate; placing a bead coated with biotin or poly-L-lysine between two-nickel plates, and compressing the bar code on the surface of the bead to form a microcake-like particle with bar code; and combining the particle with the corresponding bio-molecule thereof to produce a micro-carrier with a label. The invention also provides a test method for identifying a bio-molecule, which includes mixing several micro-carriers with the labeled unknown bio-molecules; and identifying the bar code on the micro-carrier via image recognition system, wherein the numbers and types of the known micro-carrier can be flexibly adjusted.

6 Claims, 2 Drawing Sheets

METHOD FOR PRODUCING MICRO-CARRIER AND TEST METHOD BY USING SAID MICRO-CARRIER

BACKGROUND OF THE INVENTION

1. Field of the Invention

The present invention relates to a method for preserving and testing biologically genetic information, and particularly to a micro-carrier and a test method for identifying DNA, proteins and other complementary substances by using a bar code labeled micro-carrier.

2. Description of the Related Arts

Biotechnology has been developing quickly in recent years. Various products can be produced using molecular biology, biological cells, or other metabolites thereof by this technique, which can be extensively applied in the fields of pharmaceutical, pesticide, environmental protection, process development, and aquaculture.

The combination of biotechnology with electric technology is a trend; wherein the most attractive is the biochip and DNA chip (i.e. gene chip). In addition to silicon, the material of those chips can include absorbent materials such as glass, plant cellulose, gel, and organic polymers. The gene chip has various gene fragments neatly aligned and adhered onto a nail-sized chip, in which thousands upon thousands of gene fragments are accommodated. Users can select different kinds of gene chips based on their purposes.

The principle of the aforementioned gene chip is that different groups of gene fragments are adhered onto a chip, followed by immersion into a solution containing unknown genes labeled with fluorescence. If the fluorescence-labeled gene matches the specific gene fragment on the chip, a fluorescent signal retained thereon due to complementary combination will be observed by microscopy. Therefore, the unknown gene can be identified by the complementary sequence adhered on the chip.

Under the design of large production, thousands upon thousands of gene fragments or proteins are adhered onto the chip; however, it has to avoid inaccuracy resulting from different gene fragments or proteins whose locations on the chip are too close. Thus, the precise control of the spots on the chip is very important. Moreover, the precise control requires expensive equipment, which restricts the application of the chip. Therefore, there is still a need for developing a bio-molecule database and test technique thereof, which possess advantages of more efficiency, low cost, and low limitation.

SUMMARY OF THE INVENTION

It is therefore the main purpose of the present invention to provide a convenient, inexpensive, and rapid method for producing a micro-carrier of bio-molecule (e.g. gene or protein), and a method for testing bio-molecules by using the micro-carrier.

Another purpose of the present invention is to provide a test method for identifying a bio-molecule, wherein the numbers and types of the known micro-carrier can be flexibly adjusted.

According to the method of the present invention, bar codes are patterned on a mask using an integrated circuit process; followed by exposure to a substrate coated with photoresist using photolithography. After etching and removing residual photoresist, the desired bar code can be formed on the substrate, and subsequently a nickel plate is thus electroformed. Before or after coating with bio-molecule binding material, a bead (Q-bot) is placed between two-nickel plates, and the bar code is then hot compressed onto the surface of the bead to form a microcake-like particle with bar code. Afterwards, each of the particles mentioned above are combined with the corresponding genes or proteins thereof to produce large amount of micro-carriers with labels. On the other hand, according to the method for testing bio-molecules described herein, large amounts of micro-carriers mentioned above are employed and the labeled (for example, fluorescence-labeled) unknown bio-molecules are mixed with the micro-carriers. The hybridization intensities of the fluorescence or different markers of the unknown bio-molecules thus are identified by the bar code on the micro-carrier via an image recognition system.

BRIEF DESCRIPTION OF THE DRAWINGS

The present invention will be more fully understood and further advantages will become apparent when reference is made to the following description of the invention and the accompanying drawings in which.

DETAILED DESCRIPTION OF THE INVENTION

The present invention is characterized by the combination of biotechnology with integrated circuit process to produce a bio-molecule micro-carrier. Another feature of the present invention is a method for testing unknown bio-molecules by using the micro-carrier.

The method for producing a micro-carrier of the present invention is performed as follows. A layer of bio-molecule binding material, such as biotin, poly-L-lysine, etc., was coated onto the surface of a bead. The desired individual bio-molecules (e.g. gene or protein) were represented by a corresponding bar code, wherein pluralities of the bar code were patterned on a mask using an integrated circuit process, followed by exposing to a substrate coated with photoresist using photolithography. After etching and removing residual photoresist, the bar code was formed on the substrate, and subsequently a nickel plate was thus electroformed. The aforementioned bead was placed between two-nickel plates, and the bar code facing inwards was then hot compressed onto the surface of the bead to form a microcake-like particle with the bar code. A layer of bio-molecule binding material was coated onto the particle before or after bar code patterning. Finally, the particles mentioned above were combined with the corresponding bio-molecules thereof to produce various micro-carriers of bio-molecules with labels. Therefore, users can produce a vial containing various micro-carriers with bar codes in accordance with the present invention.

The term "micro-carrier" used herein refers to a bead marked with a specific bar code, then coated with a layer of bio-molecule binding material, and then carries a corresponding bio-molecule. The material of the bead is not limited, including silicon, glass, plant cellulose, gel, and organic polymers. The size of the bead ranges from 20 μm to 200 μm in diameter, preferably less than 100 μm.

The bio-molecules used herein can include, but are not limited to, nucleic acid, oligonucleotide, peptide nucleic acid (PNA), antigen, antibody, enzyme or protein.

In the process of producing the above particles, the hemisphere particles can be alternatively formed from the beads placed between two-nickel plates by dropping a UV photosensitizer micelle, such as Arabic micelle, onto the nickel plates, followed by UV irradiation for curing.

Figure 1:
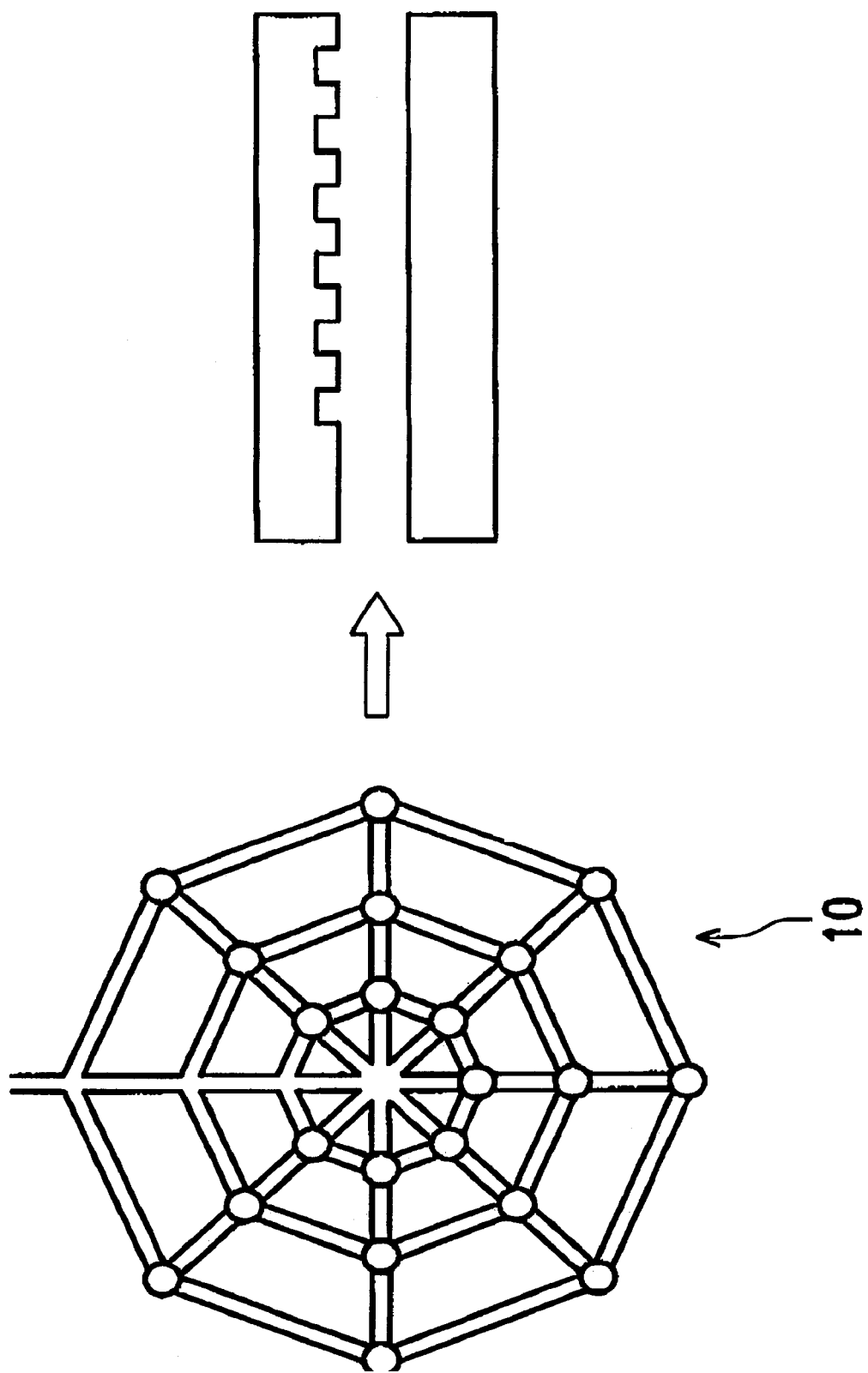
FIG. 1 is a diagram showing an insert for producing the micro-carrier of the present invention.

In addition, the cake-like pattern and bar code can be simultaneously patterned on a mask, as shown in FIG. 1, followed by etching to form a mold. The microcake-like particle can thus be molded by injection or hot compression.

Another aspect of the present invention provides a method for testing an unknown bio-molecule by using the micro-carrier mentioned above. The method is comprised of the following steps: providing a vial containing numerous micro-carriers with bar code; adding a labeled (for example, fluorescence-labeled) unknown bio-molecule to said vial and mixing (i.e. hybridizing), wherein a signal, such as fluorescence, is obtained when the micro-carrier is complementary with or recognized by the unknown bio-molecule; transferring the micro-carrier in the vial onto a transporter, wherein a microscope connected with a computer is set above the transporter; and identifying said bar code of the signaling micro-carrier by an image recognition system, thereby identifying the unknown bio-molecule.

In addition to the bar code used to identify bio-molecules, the present invention further employs the shape, size, color, etc. of the carrier as codes, which can be classified into many categories, such as: (1) Shape. The sphere bead described above can be replaced by a rectangle or polygon. For example, a certain kind of length and width can represent a specific bio-molecule, or either a triangle or polygon with sides of different length can represent different bio-molecules. (2) Size. For example, the large bead represents one bio-molecule and the small one represents another. The diameter of the bead can be used as a bio-molecule marker. (3) Color. Different colors can represent different bio-molecules. For example, red, yellow, blue, and white can be used to represent four different kinds of bio-molecules. Similarly, each micro-carrier can be identified and counted via the microscope connected with computer and the image recognition system.

Figure 2:
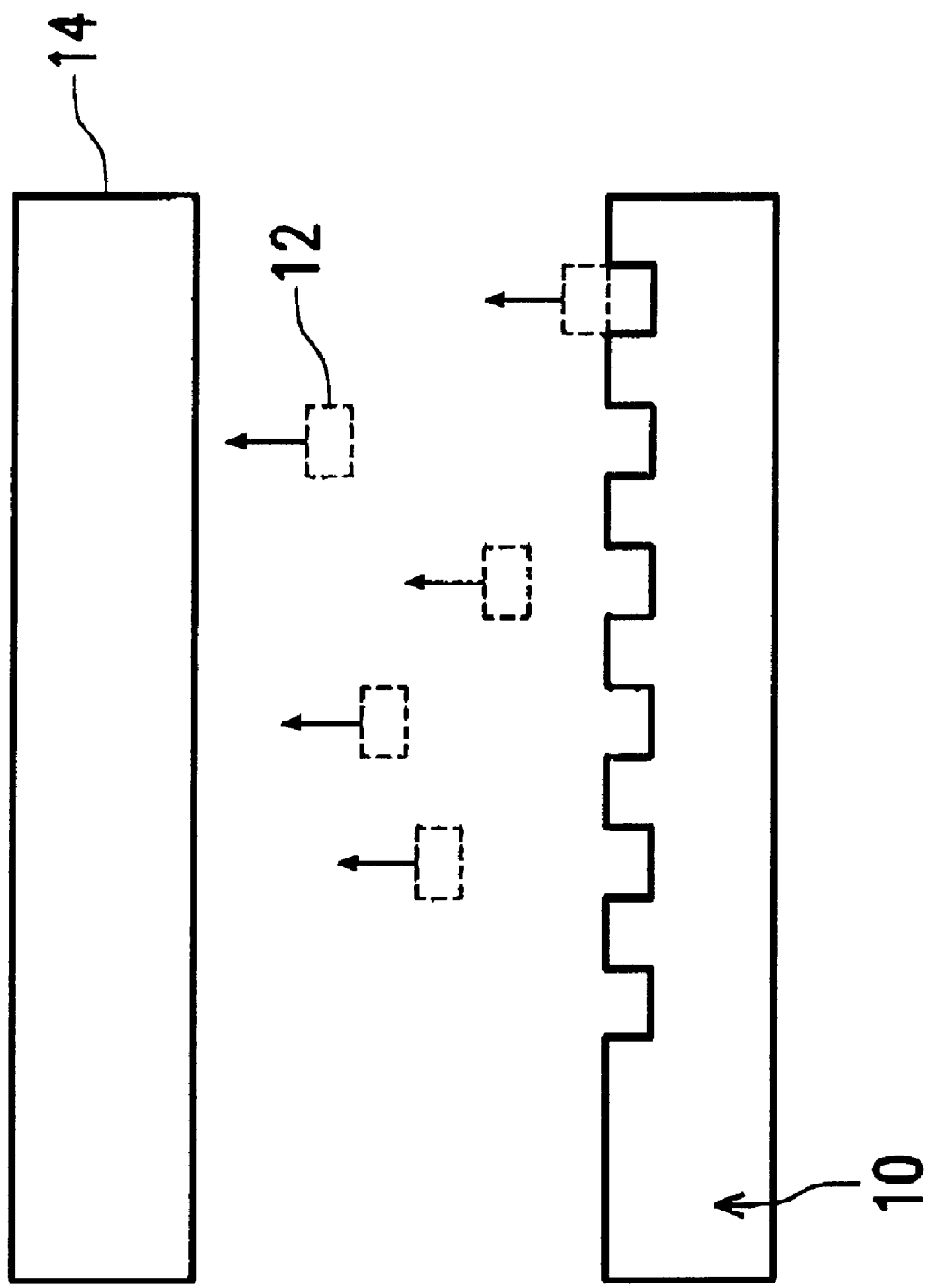
FIG. 2 is a schematic diagram showing the process for producing the micro-carrier of the present invention.

Furthermore, the insert 10 of the aforementioned carrier with different shape and/or size can also be produced by photolithography, as shown in FIG. 1, followed by injection or hot compression. The resulting particles 12 are wedged in insert 10 due to their very small size. The insert 10 can be electrified with a negative charge and the particles 12 can thus be attracted to a collection plate 14 that is electrified with a positive charge (as shown in FIG. 2). The detour among particles can be broken via rolling compression. If particles bear the detour with a broken rod, software can be employed to remove such detours during identification.

The methods of the present invention do not require expensive equipment, and a small laboratory can flexibly adjust the numbers and types of the known micro-carrier. For example, if one needs five known bio-molecules, the preparation of only five vials of micro-carriers with bar codes and mixing them into one vial is enough. On the contrary, the conventional biochip has the fixed number of genes, e.g., 1,000 genes on the chip. If the user needs only five genes thereon, the manufacturer cannot customize the chip because of the expense. Therefore, the method of the present invention possesses the advantages of convenience, flexibility, and cost-saving. A general small laboratory can accomplish the bio-molecule test itself; thus the method of the present invention can be widely applied, thereby facilitating biotechnology.

While the invention has been particularly shown and described with the reference to the preferred embodiment thereof, it will be understood by those skilled in the art that various changes in form and details may be made without departing from the spirit and scope of the invention.

What is claimed is:

1. A method for producing a micro-carrier of bio-molecule, comprising:

patterning pluralities of bar code on a mask using an integrated circuit process, wherein the bar code represents a desired bio-molecule;

exposing the bar code to a substrate coated with photoresist using photolithography;

etching and removing residual photoresist, wherein the bar code is formed on the substrate, and electroforming said substrate with the bar code to a nickel plate;

placing a bead between said nickel plate on which the bar code has been electroformed and a second nickel plate, and compressing the bar code onto the surface of said bead to form a particle with a bar code;

coating said bead with a layer of bio-molecule binding material; and combining said particle with the corresponding bio-molecule thereof to produce a micro-carrier with a label.

2. The method as claimed in claim 1, wherein said particle is formed from a bead placed between the nickel plates by dropping a UV photosensitizer micelle onto the nickel plates, followed by UV irradiation for curing.

3. The method as claimed in claim 1, wherein said particle is produced by simultaneously patterning a pattern and bar code on a mask, and molding by injection or hot compression.

4. The method as claimed in claim 1, wherein said micro-carrier is further characterized by the shape, size, or color of said micro-carrier as a code.

5. The method as claimed in claim 1, wherein the bio-molecule comprises nucleic acid, oligonucleotide, peptide nucleic acid, antigen, antibody, enzyme or protein.

6. The method as claimed in claim 1, wherein the bio-molecule binding material comprises biotin or poly-L-lysine.

\* \* \* \* \*